US012741920B2

(12) United States Patent
Tomaki et al.

(10) Patent No.: US 12,741,920 B2
(45) Date of Patent: Sep. 22, 2026

(54) ALICYCLIC ALCOHOL, ALICYCLIC ALCOHOL COMPOSITION, AND PERFUME COMPOSITION

(71) Applicant: MITSUBISHI GAS CHEMICAL COMPANY, INC., Chiyoda-ku (JP)

(72) Inventors: Keisuke Tomaki, Kanagawa (JP); Shinyou Shirai, Okayama (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 726 days.

(21) Appl. No.: 18/248,899

(22) PCT Filed: Oct. 19, 2021

(86) PCT No.: PCT/JP2021/038561
§ 371 (c)(1),
(2) Date: Apr. 13, 2023

(87) PCT Pub. No.: WO2022/085670
PCT Pub. Date: Apr. 28, 2022

(65) Prior Publication Data
US 2023/0391701 A1 Dec. 7, 2023

(30) Foreign Application Priority Data
Oct. 19, 2020 (JP) ................................. 2020-175477

(51) Int. Cl.
*C07C 31/135* (2006.01)
*C11B 9/00* (2006.01)

(52) U.S. Cl.
CPC ........ *C07C 31/1355* (2013.01); *C11B 9/0034* (2013.01)

(58) Field of Classification Search
CPC ...... A61K 8/34; A61Q 13/00; C07C 31/1355; C07C 2601/14; C07C 29/141; C11B 9/0034; C11B 9/0015; C11D 3/50
See application file for complete search history.

(56) References Cited

U.S. PATENT DOCUMENTS

| | | | | |
|---|---|---|---|---|
| 2,501,199 | A * | 3/1950 | Wearn | A23L 27/203 560/1 |
| 2009/0182177 | A1 | 7/2009 | Kotachi et al. | |
| 2011/0251439 | A1 | 10/2011 | Mirk et al. | |
| 2013/0338403 | A1* | 12/2013 | Kitamura | C07C 51/58 568/832 |
| 2019/0249103 | A1 | 8/2019 | Takegami et al. | |

FOREIGN PATENT DOCUMENTS

| | | | |
|---|---|---|---|
| CN | 101472867 | A | 7/2009 |
| CN | 102256919 | A | 11/2011 |
| EP | 0 994 177 | A2 | 4/2000 |
| GB | 1416659 | | 12/1975 |
| JP | 39-19627 | B1 | 9/1964 |
| JP | 49-56955 | A | 6/1974 |
| JP | 1-207252 | A | 8/1989 |
| JP | 2010215529 | A * | 9/2010 |
| JP | 2012-140353 | A | 7/2012 |
| JP | 2013-519638 | A | 5/2013 |
| WO | WO 2018/008667 | A1 | 1/2018 |

OTHER PUBLICATIONS

Motoichi Indo, “Zoho Kaitei ban, Gosei Koryo: Kagaku to Shohin Chishiki (Enlarged and Revised Edition, Synthetic Fragrances: Chemistry and Product Knowledge)”, The Chemical Daily Co. Ltd., 1996, p. 54 to 56 (with English Translation).
Kropp, Paul J., “Photochemistry of (+)-2-carene-4a-methanol”, Journal of the American Chemical Society, 1967, 89(5), 1126-34 p. 1130, compounds 22-23.
Watanabe, Yuichi, “Reaction of a-pinene with formaldehyde”, Nippon Kagaku Zasshi, 1960, 81, 931-3p.932, compound (with English Translation).

(Continued)

*Primary Examiner* — Angela C Brown-Pettigrew
*Assistant Examiner* — Aja Aryanna Walker
(74) *Attorney, Agent, or Firm* — Oblon, McClelland, Maier & Neustadt, L.L.P.

(57) ABSTRACT

An alicyclic alcohol of Formula (1) and a fragrance composition including the same is described. An alicyclic alcohol composition containing an alicyclic alcohol of Formula (1) and an alicyclic alcohol of Formula (2), is also described, and this composition may also include an alicyclic alcohol of Formula (3). The alicyclic alcohol composition may comprise Formula (1) at a content of 85 mass % to 98 mass %.

(1)

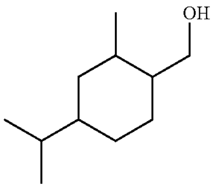

(2)

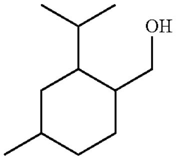

(3)

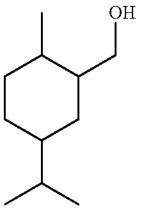

20 Claims, No Drawings

(56) References Cited

OTHER PUBLICATIONS

Falorni, Massimo et al., "Alkylmetal asymmetric reduction. 20. A reinvestigation on the stereochemistry of ketone reductions by optically active alkylmetal compounds", Journal of Organic Chemistry, 1989,54(10), 2383-8 p. 2383, compound 1b.
The Chemical Daily Co., Ltd., 2. Alcohol 2.1 Aliphatic alcohol. Synthetic fragrance: Chemistry and product knowledge, (with English Translation), pp. 71-72.
CAS Registry No. 2573599-91-2, Databaseregistry, [Online].Jan. 21, 2021, [retrieved on Nov. 16, 2021], Retrieved from: STN.
CAS Registry No. 2573599-92-3, Databaseregistry, [Online].Jan. 21, 2021, [retrieved on Nov. 16, 2021], Retrieved from: STN.

* cited by examiner

ALICYCLIC ALCOHOL, ALICYCLIC ALCOHOL COMPOSITION, AND PERFUME COMPOSITION

CROSS-REFERENCE TO RELATED APPLICATIONS

The present application is a 35 U.S.C. § 371 National Stage Application of International Patent Application PCT/JP2021/038561, filed Oct. 19, 2021, which is based on and claims the benefit of priority to Japanese Application No. 2020-175477, filed Oct. 19, 2020. The entire contents of these applications are incorporated herein by reference.

TECHNICAL FIELD

The present invention relates to an alicyclic alcohol, a method for producing the same, and an alicyclic alcohol composition containing the alicyclic alcohol, and a fragrance composition.

BACKGROUND ART

Some alicyclic alcohols are known to be useful as fragrance ingredients. For example, Non-Patent Literature 1 discloses that p-isopropylcyclohexylmethanol (Mayol) having a floral scent; p-isopropylcyclohexanol having a floral scent of lilac, rose, and geranium, with mint added; 2,4-dimethyl-3-cyclohexene-1-methanol having a fresh green floral scent reminiscent of hyacinth and muguet; and the like are useful as fragrance ingredients, and describes their applications, such as skin care products.

In addition, Patent Document 1 discloses an alicyclic alcohol compound having an excellent floral-green-like fragrance with a refreshing and fresh feeling.

CITATION LIST

Non-Patent Literature

Non-Patent Literature 1: Motoichi Indo, "Zoho Kaitei ban, Gosei Koryo: Kagaku to Shohin Chishiki (Enlarged and Revised Edition, Synthetic Fragrances: Chemistry and Product Knowledge)", The Chemical Daily Co. Ltd., 1996, p. 54 to 56

Patent Document

Patent Document 1: JP 2012-140353 A

SUMMARY OF INVENTION

Technical Problem

Alicyclic alcohols used as fragrances are used in various fields, such as cosmetic products including skin care products as described above, as well as fragrance products, detergents, sundry goods, pharmaceuticals, and food products. To increase the value of the end products, new scents are being developed, and fragrances having a novel scent are in demand.

Thus, an object of the present invention is to provide an alicyclic alcohol that has a complex scent including floral notes of muguet, jasmine, and rose as well as a soft woody note in a lasting scent and has excellent lasting scent properties, can further impart diffusibility to floral and woody notes in a fragrance composition, and is useful as a fragrance and also useful as a fragrance ingredient.

Solution to Problem

The present inventors have synthesized and/or blended various alicyclic alcohols and compositions containing a plurality of those alicyclic alcohols and evaluated their fragrances, and found that specific alicyclic alcohols and compositions containing those alicyclic alcohols have an excellent fragrance note and are also excellent as fragrance ingredients, and completed the present invention.

That is, the present invention is as follows.

[1] An alicyclic alcohol represented by Formula (1):

(1)

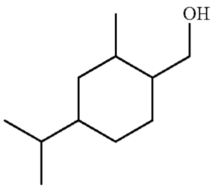

[2] A fragrance composition containing the alicyclic alcohol described in [1].

[3] An alicyclic alcohol composition containing an alicyclic alcohol represented by Formula (1) and an alicyclic alcohol represented by Formula (2):

(1)

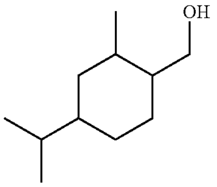

(2)

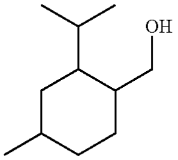

[4] The alicyclic alcohol composition according to [3], further containing an alicyclic alcohol represented by Formula (3):

(3)

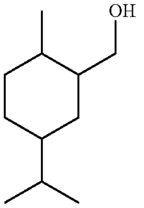

[5] The alicyclic alcohol composition according to [3] or [4], wherein a total content of the alicyclic alcohol represented by Formula (1) and the alicyclic alcohol represented by Formula (2) is 95 mass % or higher.

[6] The alicyclic alcohol composition according to any one of [3] to [5], wherein a content of the alicyclic alcohol represented by Formula (1) is 85 mass % or higher and 98 mass % or lower.

[7] The alicyclic alcohol composition according to any one of [3] to [6], wherein a mass ratio [(1)/(2)] of the alicyclic alcohol represented by Formula (1) and the alicyclic alcohol represented by Formula (2) in the alicyclic alcohol composition is from 85/15 to 98/2.

[8] A fragrance composition containing the alicyclic alcohol composition described in any one of [3] to [7].

[9] An alicyclic alcohol represented by Formula (2):

(2)

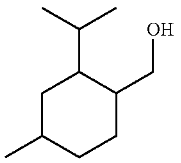

[10] A fragrance composition containing the alicyclic alcohol described in [9].

[11] A method for producing an alicyclic alcohol, the method including hydrogenating an aromatic aldehyde represented by General Formula (4) to obtain an alicyclic alcohol represented by General Formula (5):

(4)

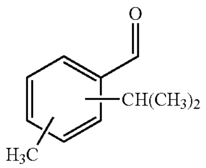

(5)

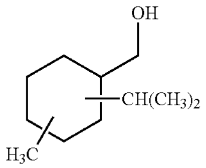

Advantageous Effects of Invention

According to the present invention, there can be provided an alicyclic alcohol that has a complex scent including floral notes of muguet, jasmine, and rose as well as a soft woody note in a lasting scent and has excellent lasting scent properties, and thus is useful as a fragrance; can further impart diffusibility to floral and woody notes in a fragrance composition and thus is also useful as a fragrance ingredient.

DESCRIPTION OF EMBODIMENTS

[Alicyclic Alcohol Represented by Formula (1)]

The following alicyclic alcohol represented by Formula (1) according to the present invention is (4-isopropyl-2-methylcyclohexyl) methanol:

(1)

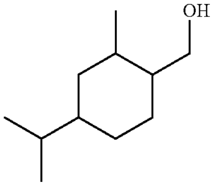

The alicyclic alcohol represented by Formula (1) has a complex scent including floral notes of muguet, jasmine, and rose as well as a soft woody note in a lasting scent, and has excellent lasting scent properties, and thus is useful as a fragrance. In addition, the alicyclic alcohol represented by Formula (1) can impart diffusibility to floral and woody notes in a fragrance composition and thus is also useful as a fragrance ingredient.

The alicyclic alcohol represented by Formula (1) is preferably obtained by a production method described later.

[Alicyclic Alcohol Composition]

An alicyclic alcohol composition of the present invention contains an alicyclic alcohol represented by Formula (1) below and an alicyclic alcohol represented by Formula (2) below. The alicyclic alcohol represented by Formula (1) below is (4-isopropyl-2-methylcyclohexyl) methanol described above.

(1)

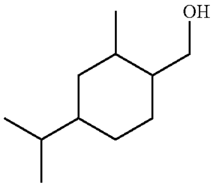

(2)

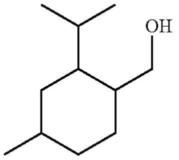

<Alicyclic Alcohol Represented by Formula (2)>

The alicyclic alcohol represented by Formula (2) and contained in the alicyclic alcohol composition of the present invention is (2-isopropyl-4-methylcyclohexyl) methanol. The alicyclic alcohol represented by Formula (2) is also useful as a fragrance.

Composition of Alicyclic Alcohol Composition, Etc.

A total content of the alicyclic alcohol represented by Formula (1) and the alicyclic alcohol represented by Formula (2) in the alicyclic alcohol composition of the present invention is preferably 95 mass % or higher, more preferably 96 mass % or higher, and even more preferably 97 mass % or higher. The upper limit is not limited except that it is to be 100 mass % or lower.

The content of the alicyclic alcohol represented by Formula (1) in the alicyclic alcohol composition of the present invention is preferably 85 mass % or higher, more preferably 87 mass % or higher, and even more preferably 90 mass % or higher, and preferably 98 mass % or lower, more preferably 97 mass % or lower, and even more preferably 95 mass % or lower.

The content of the alicyclic alcohol represented by Formula (2) in the alicyclic alcohol composition of the present invention is preferably 2 mass % or higher and more preferably 5 mass % or higher, and preferably 15 mass % or lower, more preferably 13 mass % or lower, and even more preferably 10 mass % or lower.

A mass ratio [(1)/(2)] of the alicyclic alcohol represented by Formula (1) and the alicyclic alcohol represented by Formula (2) in the alicyclic alcohol composition of the present invention is preferably from 85/15 to 98/2, more preferably from 87/13 to 97/3, even more preferably from 87/13 to 95/5, and still more preferably from 90/10 to 95/5.

The alicyclic alcohol composition of the present invention may further contain an alicyclic alcohol represented by Formula (3) below:

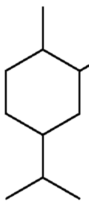

(3)

When the alicyclic alcohol composition of the present invention contains the alicyclic alcohol composition represented by Formula (3), the content of the alicyclic alcohol represented by Formula (3) in the composition is preferably 0.1 mass % or higher and more preferably 1 mass % or higher, and preferably 3 mass % or lower and more preferably 2 mass % or lower.

The alicyclic alcohol composition of the present invention having the composition described above has a scent including floral notes of muguet, jasmine, and rose as well as a woody note in a lasting scent and is useful as a fragrance. In addition, the alicyclic alcohol composition of the present invention is also useful as a fragrance ingredient (a fragrance ingredient of a fragrance composition) and can be used as a fragrance component of various products.

[Fragrance Composition]

A fragrance composition of the present invention contains the alicyclic alcohol or the alicyclic alcohol composition.

That is, a fragrance composition of a first embodiment of the present invention contains the alicyclic alcohol represented by Formula (1) below:

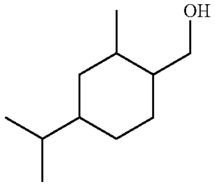

(1)

The content of the alicyclic alcohol in the fragrance composition of the present invention is to be appropriately adjusted according to the type of fragrance composition, the type of target fragrance, the intensity of the fragrance, and the like and is preferably from 0.01 to 90 mass % and more preferably from 0.1 to 50 mass %.

In addition, a fragrance composition of a second embodiment of the present invention contains the alicyclic alcohol composition containing the alicyclic alcohol represented by Formula (1) below and the alicyclic alcohol represented by Formula (2) below:

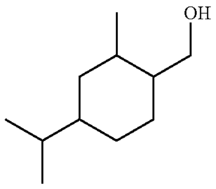

(1)

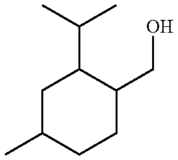

(2)

A mass ratio [(1)/(2)] of the alicyclic alcohol represented by Formula (1) and the alicyclic alcohol represented by Formula (2) in the fragrance composition of the second embodiment of the present invention is preferably from 85/15 to 98/2, more preferably from 87/13 to 97/3, even more preferably from 87/13 to 95/5, and still more preferably from 90/10 to 95/5.

Furthermore, the fragrance composition of the second embodiment of the present invention may further contain the alicyclic alcohol represented by Formula (3) below:

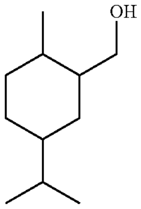

(3)

The content of the alicyclic alcohol composition in the fragrance composition of the present invention is to be appropriately adjusted according to the type of fragrance composition, the type of target fragrance, the intensity of the fragrance, and the like and is preferably from 0.01 to 90 mass % and more preferably from 0.1 to 50 mass %.

Examples of the fragrance components that can be used in combination with the alicyclic alcohol or the alicyclic alcohol composition include, but are not limited to, surfactants, such as polyoxyethylene lauryl sulfate ether; solvents, such as dipropylene glycol, diethyl phthalate, ethylene glycol, propylene glycol, methyl myristate, and triethyl citrate; hydrocarbons, such as limonene, α-pinene, β-pinene, terpinene, cedrene, longifolene, and valencene; alcohols, such as linalool, citronellol, geraniol, nerol, terpineol, dihydromyrcenol, ethyllinalool, famesol, nerolidol, cis-3-hexenol, menthol, borneol, B3-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten- 1-yl)-2-buten-1-ol, isocamphylcyclohexanol, and 3,7-dimethyl-7-methoxyoctane-2-ol; phenols, such as eugenol, thymol, and vanillin; esters, such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and frutate; aldehydes, such as n-octanal, n-decanal, n-dodecanal, 2-methylundecanal, 10-undecenal, citronellal, citral, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones, such as methylheptenone, 4-methylene-3,5,6,6-tetramethyl-2-heptanone, amylcyclopentanone, 3-methyl-2-(cis-2-pentene-1-yl)-2-cyclopenten-1-one, methylcyclopentenolone, rose ketones, γ-methylionone, α-ionone, carbone, menthone, camphor, nootkatone, benzylacetone, anisylacetone, methyl-p-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals, such as acetoaldehyde ethylphenylpropyl acetal, citraldiethyl acetal, phenylacetoaldehyde glycerin acetal, and ethylacetoacetate ethyleneglycol ketals; ethers, such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2, 1-b]furane; nitriles such as citronellyl nitrile; lactones, such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; and other fragrance materials, such as natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, vetiver, patchouli, and labdanum. One of these other fragrance materials may be individually blended or two or more of them may be blended.

The fragrance composition of the present invention can be used as a fragrance component in various products, such as perfumes and cosmetics, health and hygiene materials, sundry goods, beverages, food products, quasi-drugs, and pharmaceuticals, to improve the fragrance of the product to which the fragrance composition is blended.

The fragrance composition of the present invention can be used as a fragrance component, for example, in fragrance products, such as perfumes and colognes; cosmetics for hair, such as shampoos, rinses, hair tonics, hair creams, mousses, gels, pomades, sprays; cosmetics for skin, such as lotions, beauty essences, creams, emulsions, packs, foundations, face powders, lipsticks, and makeup cosmetics; products for hygiene, such as dish washing detergents, laundry washing detergents, house detergents, glass cleaners, softeners, bleaching agents, fragrances, and insecticides; quasi-drugs, such as toothpastes, mouthwashes, bath additives, antiperspirants, and permanent wave agents; sundry goods, such as paper products; pharmaceuticals; and food products.

The content of the fragrance composition of the present invention in the above products is to be appropriately adjusted according to the intensity of the fragrance required for each product and the like and is preferably from 0.001 to 50 mass % and more preferably from 0.01 to 20 mass %.

In addition, a fragrance composition of a third embodiment of the present invention contains the alicyclic alcohol represented by Formula (2). The alicyclic alcohol represented by Formula (2) is also useful as a fragrance ingredient (a fragrance ingredient of a fragrance composition), and the content of the alicyclic alcohol represented by Formula (2) in the fragrance composition is preferably from 0.01 to 90 mass % and more preferably from 0.1 to 50 mass %. Examples of the fragrance component that can be used in combination with the alicyclic alcohol include those described above.

Furthermore, the content of the fragrance composition in each of these products is preferably from 0.001 to 50 mass % and more preferably from 0.01 to 20 mass %.

[Method for Producing Alicyclic Alcohol and Method for Producing Alicyclic Alcohol Composition]

The alicyclic alcohol constituting the alicyclic alcohol composition of the present invention may be obtained by any production method but is preferably obtained by a production method in which an aromatic aldehyde represented by General Formula (4) below is hydrogenated to produce an alicyclic alcohol represented by General Formula (5) below:

(4)

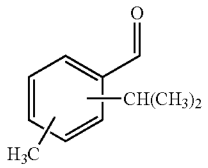

(5)

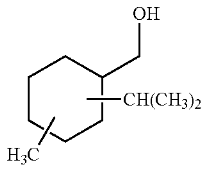

Here, the aromatic aldehyde represented by General Formula (4) includes an aromatic aldehyde represented by Formula (4-1) below, an aromatic aldehyde represented by Formula (4-2), and an aromatic aldehyde represented by Formula (4-3) below:

(4-1)

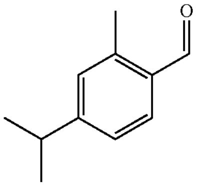

-continued (4-2)

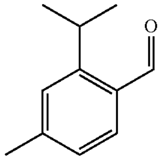

(4-3)

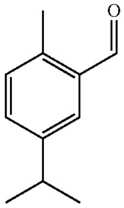

According to the present production method, the alicyclic alcohol represented by Formula (1) can be obtained from the aromatic aldehyde represented by Formula (4-1), the alicyclic alcohol represented by Formula (2) can be obtained from the aromatic aldehyde represented by Formula (4-2), and the alicyclic alcohol represented by Formula (3) can be obtained from the aromatic aldehyde represented by Formula (4-3).

The alicyclic alcohol composition of the present invention contains the alicyclic alcohol represented by Formula (1) and the alicyclic alcohol represented by Formula (2), but the composition may be directly obtained by hydrogenating a mixture of the aromatic aldehyde represented by Formula (4-1) and the aromatic aldehyde represented by Formula (4-2) as a raw material, or the composition may be obtained by obtaining each alicyclic alcohol and then mixing them.

The alicyclic alcohol represented by General Formula (5) includes the alicyclic alcohol represented by Formula (1), the alicyclic alcohol represented by Formula (2), and the alicyclic alcohol represented by Formula (3).

The aromatic aldehyde represented by General Formula (4) to be used as a raw material for the hydrogenation reaction may be obtained by any method but is preferably synthesized from cymene (isopropyltoluene) by formylation using a super-strong acid as shown in the following formula:

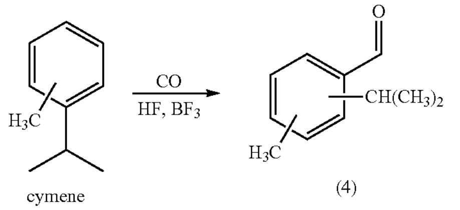

cymene (4)

The formylation to obtain the aromatic aldehyde represented by Formula (4) to be used in the production method of the present invention is preferably a method in which carbon monoxide is reacted with cymene in the presence of a super-strong acid and is specifically preferably a method in which carbon monoxide is reacted with cymene in the presence of a Brønsted acid and a Lewis acid, such as $HF/BF_3$.

When $HF/BF_3$ is used as a Brønsted acid and a Lewis acid, the amount of HF to be used is preferably from 5 to 25 mol times the amount of raw material cymene, and the amount of $BF_3$ to be used is preferably from 0.2 to 2.5 mol times the amount of raw material cymene.

The reaction temperature is preferably from −30 to 10° C.

The reaction is preferably carried out under pressure, and the reaction pressure is preferably from 1.0 to 3.0 MPaG.

The reaction time is preferably from 0.2 to 5 hours.

The aromatic aldehyde represented by Formula (4-1) is obtained in high yield using m-cymene as the cymene used as a raw material, but the aromatic aldehyde represented by Formula (4-1) can also be obtained in high yield from p-cymene by formylation according to the above reaction conditions.

Formylation using p-cymene produces the aromatic aldehyde represented by Formula (4-2) as a by-product. Thus, an aromatic aldehyde mixture containing the aromatic aldehyde represented by Formula (4-1) and the aromatic aldehyde represented by Formula (4-2) to be used as a raw material for the alicyclic alcohol composition of the present invention can be obtained using p-cymene as a raw material.

p-Cymene is inexpensively available compared with m-cymene, and thus the aromatic aldehyde represented by Formula (4-1), which is a raw material for the alicyclic alcohol represented by Formula (1), is preferably obtained in high purity by formylation of p-cymene or a mixture of p-cymene and m-cymene to obtain an aromatic aldehyde mixture containing the aromatic aldehyde represented by Formula (4-1) as the main product and distillation of this.

In addition, it is also preferred to formylate p-cymene or a mixture of p-cymene and m-cymene to obtain an aromatic aldehyde mixture containing the aromatic aldehyde represented by Formula (4-1) and the aromatic aldehyde represented by Formula (4-2) and use the mixture as is as a raw material for the alicyclic alcohol composition containing the alicyclic alcohol represented by Formula (1) and the alicyclic alcohol represented by Formula (2).

A method of adjusting the ratio in the aromatic aldehyde mixture is to adjust the ratio of the raw materials, m-cymene and p-cymene, and/or adjust the conditions of the formylation reaction using p-cymene. The ratio in the resulting aromatic aldehyde mixture may be adjusted by distillation. The aromatic aldehyde mixture containing the aromatic aldehyde represented by Formula (4-1) and the aromatic aldehyde represented by Formula (4-2) in any ratio can be thus obtained. In addition, the aromatic aldehyde represented by Formula (4-3) is contained as a byproduct.

The aromatic aldehyde or the aromatic aldehyde mixture thus obtained may be used as is in the hydrogenation reaction, but the target aromatic aldehyde may be purified to increase the purity and/or to adjust to the target ratio.

The reaction conditions of the hydrogenation reaction in the production method of the present invention are not particularly limited, but it is preferred to place the aromatic aldehyde or the aromatic aldehyde mixture described above, a hydrogenation catalyst, and as necessary a solvent and the like in a pressure vessel and to introduce hydrogen.

The hydrogenation catalyst to be used in the present reaction is any typical metal catalyst used in a hydrogenation. Specific examples include ruthenium catalysts, palladium catalysts, platinum catalysts, cobalt catalysts, and nickel catalysts. From the viewpoint of being able to simultaneously hydrogenate the aromatic ring and the aldehyde group, the hydrogenation catalyst is preferably at least one selected from the group consisting of ruthenium catalysts, palladium catalysts, and platinum catalysts and more preferably a ruthenium catalyst.

The support of the metal catalyst includes activated carbon, alumina, and diatomite, and is preferably activated carbon.

In the present reaction, a solvent may be used, and a solvent that does not affect hydrogenation reaction of an alicyclic hydrocarbon compound and a saturated aliphatic hydrocarbon compound is preferably used. However, a solvent is preferably not substantially used as this can eliminate the need for removing the solvent.

The hydrogen to be used in the present reaction need not be particularly purified, and an industrial grade hydrogen may be used. The hydrogen pressure during the reaction is preferably from 2.0 to 20.0 MPa, more preferably from 3.0 to 15.0 MPa, and even more preferably from 5.0 to 10.0 MPa.

The reaction temperature is preferably from 80 to 150° C. and more preferably from 110 to 140° C. Carrying out the reaction in these ranges can prevent hydrogenation degradation of a hydroxy group and produce a target product in high yield; thus, this is preferred.

The hydrogenation reaction is preferably carried out to simultaneously hydrogenate the aromatic ring and the aldehyde group and obtain the target alicyclic alcohol or alicyclic alcohol composition in one pot, but the reaction may be divided into two stages to hydrogenate the aromatic ring and the aldehyde group separately.

The alicyclic alcohol or alicyclic alcohol composition thus obtained is preferably purified by distillation. The distillation conditions are to be appropriately adjusted by the pressure and temperature during the distillation.

The alicyclic alcohol represented by Formula (1), the alicyclic alcohol represented by Formula (2), or the alicyclic alcohol composition containing both the alicyclic alcohol represented by Formula (1) and the alicyclic alcohol represented by Formula (2) can thus be obtained. These can each be used as a fragrance but can also be mixed in any ratio and used. Among others, the alicyclic alcohol composition containing the alicyclic alcohol represented by Formula (1) and the alicyclic alcohol represented by Formula (2) in the above ratio is preferred.

The resulting alicyclic alcohol represented by Formula (1) has a complex scent including floral notes of muguet, jasmine, and rose as well as a soft woody note in a lasting scent and is useful as a fragrance. Furthermore, the resulting alicyclic alcohol represented by Formula (1) can impart lasting scent properties and diffusibility to a fragrance composition and thus is useful as a fragrance ingredient (a fragrance ingredient of a fragrance composition). In addition, the alicyclic alcohol represented by Formula (2) is also useful as a fragrance. Furthermore, the alicyclic alcohol composition containing both the alicyclic alcohol represented by Formula (1) and the alicyclic alcohol represented by Formula (2) has a scent including floral notes of muguet, jasmine, and rose as well as a woody note in a lasting scent and is useful as a fragrance.

EXAMPLES

The present invention will be described specifically based on Examples described below, but the present invention is not limited to these Examples.

<Gas Chromatographic Analysis Method (Composition Ratio)>

Composition ratios of products obtained in production examples and examples were determined by a gas chromatographic method according to the following conditions.

- Instrument: Gas Chromatography Nexis GC-2030 (available from Shimadzu Corporation)
- Column: DB-1 (30 m in length, 0.53 mm in inner diameter, and 1.5 μm in film thickness)

- Detector: FID (H2 30 mL/min, Air 300 mL/min)
- Carrier gas: He (constant flow; average linear velocity 38 cm/sec)
- Split ratio: 28.1
- Injection port temperature: 300° C.
- Detector temperature: 300° C.
- Injection volume: 1.0 μL
- Oven temperature: The temperature was raised from 50° C. to 150° C. at 5° C./min, then raised to 280° C. at 10° C./min after reaching 150° C., and then maintained for 7 minutes. The temperature was then raised to 300° C. at 10° C./min and maintained for 5 minutes.

<NMR Analysis Method (Structure of Compound)>

NMR analysis was performed on an alicyclic alcohol obtained in Example 2 under the following conditions.

- Instrument used: Varian NMR System PS600 600 MHz NMR spectrometer
- Resonance frequency: 600 MHz
- Measurement temperature: room temperature
- Measurement range: $-2 \leq \delta \leq 14$
- Solvent: $CDCl_3$
- Chemical shift reference material: $CHCl_3$ in $CDCl_3$ ($\delta = 7.26$)

<GC-MS Analysis Method (Structure of Compound)>

GC-MS analysis was performed on an alicyclic alcohol obtained in Example 2 under the following conditions.

(GC Side)

- Instrument used: Gas Chromatography GC2010 Plus (available from Shimadzu Corporation)
- Column: DB-1MS (30 m in length, 0.25 mm in inner diameter, and 0.25 μm in film thickness)
- Injection volume: 1 μL
- Gasification chamber temperature: 300° C.
- Carrier gas: He
- Linear velocity control: 38.0 cm/s
- Split ratio: 28.1
- Oven temperature: The temperature was raised from 50° C. to 150° C. at 5° C./min, then raised to 280° C. at 10° C./min after reaching 150° C., and then maintained for 7 minutes. The temperature was then raised to 300° C. at 10° C./min and maintained for 5 minutes.

(MS Side)

- Instrument used: GCMS-QP2010 Ultra (available from Shimadzu Corporation)
- Fragmentation method: EI
- Ion source temperature: 200° C.
- Interface temperature: 250° C.
- Detector voltage: 0.8 kV

Production Example 1 (Production of Aromatic Aldehyde Mixture)

As the formylation reactor, used was a 500-mL autoclave equipped with a NAC drive-type stirrer and 3 inlet nozzles at the top and 1 outlet nozzle at the bottom, the internal temperature of which autoclave was controllable with a jacket. A refrigerant was allowed to flow through the jacket, and 126.5 g (6.32 mol) of hydrogen fluoride was placed in the autoclave cooled to −25° C. Thereafter, 42.6 g (0.63 mol) of boron trifluoride was added with stirring while the temperature was adjusted not to exceed −25° C. After boron trifluoride was added, the pressure was raised to 2 MPaG with carbon monoxide while the temperature in the autoclave was maintained at −25° C., and 56.7 g (0.42 mol) of m-, p-mixed cymene (isopropyltoluene, m:p (molar ratio)=68.3:31.7) was added.

After stirred for 45 minutes while the temperature of −25° C. and the pressure of 2 MPaG were maintained, the reaction mixture in the autoclave was extracted into ice water. The extracted mixture was shaken well, and then the oil layer was separated. The resulting oil layer part was washed with water, and a crude aromatic aldehyde mixture was obtained.

Low-boiling point components were removed from the resulting crude aromatic aldehyde mixture using a distillation column with a theoretical plate number of 20 stages. Low-boiling point components were distilled off at a distillation column pressure of 15 torr until the distillation temperature reached 126° C., and a distillate was collected from the time when the distillation temperature of 126° C. was reached, and an aromatic aldehyde mixture containing 4-isopropyl-2-methylbenzaldehyde (Formula (4-1)), 2-isopropyl-4-methylbenzaldehyde (Formula (4-2)), 5-isopropyl-2-methylbenzaldehyde (Formula (4-3)) in a mass ratio of 91:7:2 was obtained.

Example 1 (Production of Alicyclic Alcohol Composition)

A hydrogenation reaction was carried out using the aromatic aldehyde mixture obtained in Production Example 1.

In a 500-mL autoclave were placed 150.0 g of the aromatic aldehyde mixture and 16.5 g (dry weight of 7.5 g) of a 5 mass % Ru/C catalyst with a water content of 54.7%, and the inside of the reactor was purged with nitrogen and hydrogen. Then, hydrogen was introduced to give a hydrogen pressure of 8.0 MPa, the reaction was carried out with stirring at a reaction temperature of 140° C. for six hours, and an alicyclic alcohol composition was obtained. The end point of the reaction was a point when the consumption of hydrogen ended.

The resulting alicyclic alcohol composition was an alicyclic alcohol composition containing (4-isopropyl-2-methylcyclohexyl) methanol (Formula (1)), (2-isopropyl-4-methylcyclohexyl) methanol (Formula (2)), and (5-isopropyl-2-methylcyclohexyl) methanol (Formula (3)) in a mass ratio of 91:7:2.

The resulting alicyclic alcohol composition had a scent including floral notes of muguet, jasmine, and rose as well as a woody note in a lasting scent.

Example 2 (Production of Alicyclic Alcohol)

First, an alicyclic alcohol composition was obtained in the same manner as in Example 1.

The resulting alicyclic alcohol composition was rectified using a rectification column with a theoretical plate number of 200 stages (a distillate temperature of 121° C. and a vacuum level of 10 torr), and an alicyclic alcohol (4-isopropyl-2-methylcyclohexyl) methanol (Formula (1)) was obtained with a purity of 98.5 mass %.

The resulting alicyclic alcohol had a complex scent including floral notes of muguet, jasmine, and rose as well as a soft woody note, such as that of sandalwood, in a lasting scent.

Analytical results of the alicyclic alcohol (4-isopropyl-2-methylcyclohexyl) methanol (Formula (1) are shown below.

(NMR Analysis Results)

$^1$H NMR (600 MHz, $CDCl_3$) δ 2H 3.72 (dd, J=4.8 and 10.8 Hz), 3.59 (dd, J=9.9 Hz), 3.42 to 3.52 (m); 1H 2.05 to 2.15 (m), 1.97 (dq, J=3.2 and 13.5 Hz), 1.86 (dq, J=3.4 and 12.6); 3H 0.94 (d, J=7.2 Hz); 6H 0.85 (dd, J=1.2 and 6.6 Hz); 9H 0.90 to 1.80 (m)

(GC-MS Analysis Results)

GC-MS m/z=152 (3), 137 (5), 124 (5), 109 (100), 95 (19), 83 (52), 67 (61), 55 (53)

Example 3 and Comparative Examples 1 to 2 (Dafne-Type Fragrance Compositions)

To each of fragrance composition bases (dafne-type) shown in Table 1, 10 parts by mass of the alicyclic alcohol obtained in Example 2 was added, and a fragrance evaluation was performed. A fragrance composition prepared by adding 10 parts by mass of dipropylene glycol in place of the alicyclic alcohol was used as Comparative Example 1, and a fragrance composition prepared by adding 10 parts by mass of hydroxycitronellal (3,7-dimethyl-7-hydroxyoctanal, having a floral note of muguet) in place of the alicyclic alcohol was used as Comparative Example 2. These were evaluated for the fragrance in the same manner as the fragrance composition of Example 3 and compared with the fragrance composition of Example 3.

TABLE 1

| Blended components | Example 3 (parts by mass) | Comparative Example 1 (parts by mass) | Comparative Example 2 (parts by mass) |
|---|---|---|---|
| Alicyclic alcohol (Example 2) | 10 | — | — |
| Hydroxycitronellal | — | — | 10 |
| Dipropylene glycol | 5.54 | 15.54 | 5.54 |
| n-Undecanal | 0.04 | 0.04 | 0.04 |
| Benzyl aldehyde | 0.3 | 0.3 | 0.3 |
| Benzyl acetate | 0.7 | 0.7 | 0.7 |
| Benzyl salicylate | 4 | 4 | 4 |
| 3-(4-Methoxyphenyl)-2-methylpropanal | 0.4 | 0.4 | 0.4 |
| cis-3-Hexenol | 0.05 | 0.05 | 0.05 |
| 3,7-Dimethyl-2,6-octadienal | 0.3 | 0.3 | 0.3 |
| Citronellal | 0.3 | 0.3 | 0.3 |
| Citronellol | 4 | 4 | 4 |
| Ethylene brassylate | 24 | 24 | 24 |
| Floraline | 5 | 5 | 5 |
| Hedione | 12 | 12 | 12 |
| Helional | 0.5 | 0.5 | 0.5 |
| Indole | 0.04 | 0.04 | 0.04 |
| α-Indole | 1.2 | 1.2 | 1.2 |
| Linalool | 10 | 10 | 10 |
| Methyl anthranilate | 0.03 | 0.03 | 0.03 |
| γ-Methylionone | 0.7 | 0.7 | 0.7 |
| Nerol | 2.5 | 2.5 | 2.5 |

TABLE 1-continued

| Blended components | Example 3 (parts by mass) | Comparative Example 1 (parts by mass) | Comparative Example 2 (parts by mass) |
|---|---|---|---|
| Orange terpene | 6 | 6 | 6 |
| β-Naphthyl methyl ketone | 0.4 | 0.4 | 0.4 |
| 2-Phenylethyl alcohol | 4.5 | 4.5 | 4.5 |
| Romandolide | 5 | 5 | 5 |
| Sandela | 2.5 | 2.5 | 2.5 |
| Total | 100 | 100 | 100 |

The fragrance composition of Example 3 had an enhanced jasmine-like floral fragrance with a soft woody note imparted compared with the fragrance composition of Comparative Example 1.

In addition, the fragrance composition of Example 3 had a thick structure of overall scent compared with the fragrance composition of Comparative Example 2. Furthermore, in the fragrance composition of Example 3, a soft woody note was imparted compared with the fragrance composition of Comparative Example 2. The fragrance composition of Comparative Example 2 had an enhanced floral note of muguet compared with the fragrance composition of Comparative Example 1.

Example 4 and Comparative Examples 3 to 4 (Citrus Woody Fragrance Compositions)

To each of fragrance composition bases (citrus woody) shown in Table 2, 12 parts by mass of the alicyclic alcohol obtained in Example 2 was added, and a fragrance evaluation was performed. A fragrance composition prepared by adding 12 parts by mass of dipropylene glycol in place of the alicyclic alcohol was used as Comparative Example 3, and a fragrance composition prepared by adding 12 parts by mass of cedrol (octahydro-3,6,8,8-tetramethyl-1H, having a woody note of cedarwood) in place of the alicyclic alcohol was used as Comparative Example 4.

TABLE 2

| Blended components | Example 4 (parts by mass) | Comparative Example 3 (parts by mass) | Comparative Example 4 (parts by mass) |
|---|---|---|---|
| Alicyclic alcohol (Example 2) | 12 | — | — |
| Cedrol | — | — | 12 |
| Dipropylene glycol | 24.04 | 36.04 | 24.04 |
| Camphor | 0.03 | 0.03 | 0.03 |
| Cedarwood Virginia | 1.2 | 1.2 | 1.2 |
| cis-3-Hexenol | 1.2 | 1.2 | 1.2 |
| Citral dimethyl acetal | 0.2 | 0.2 | 0.2 |
| γ-Decalactone | 0.8 | 0.8 | 0.8 |
| Dimethyl anthranilate | 0.03 | 0.03 | 0.03 |
| Elemi resinoid | 1.4 | 1.4 | 1.4 |
| Ethyl 2-methylbutyrate | 0.06 | 0.06 | 0.06 |
| Oxacyclohexadecan-2-one | 0.1 | 0.1 | 0.1 |
| γ-Terpinene | 2 | 2 | 2 |
| Geraniol | 2.5 | 2.5 | 2.5 |
| Geranyl acetate | 0.3 | 0.3 | 0.3 |
| Grapefruit oil | 13 | 13 | 13 |
| Lemon oil | 10 | 10 | 10 |
| Lime terpene | 8 | 8 | 8 |
| Linalool | 20 | 20 | 20 |
| Linalyl acetate | 0.3 | 0.3 | 0.3 |
| β-Pinene | 2.5 | 2.5 | 2.5 |
| Tagetes oil | 0.04 | 0.04 | 0.04 |
| α-Terpineol | 0.3 | 0.3 | 0.3 |
| Total | 100 | 100 | 100 |

The fragrance composition of Example 4 had an amplified feeling of citrus woody fruit juice and an enhanced soft woody note, such as that of sandalwood, and had high diffusibility of the scent and lasting scent properties compared with the fragrance composition of Comparative Example 3.

In addition, the fragrance composition of Comparative Example 4 had an enhanced woody note compared with the fragrance composition of Comparative Example 3, but the fragrance composition of Example 4 had a further enhanced soft woody note, such as that of sandalwood, than the fragrance composition of Comparative Example 4, and the fragrance composition of Example 4 had an amplified feeling of citrus woody fruit juice and had high diffusibility of the scent and lasting scent properties.

As shown in Example 2, the alicyclic alcohol represented by Formula (1) of the present invention is found to have a complex scent including floral notes as well as a soft woody note in a lasting scent and have excellent lasting scent properties, and thus to be useful as a fragrance.

The fragrance compositions of Examples 3 and 4 are found to have enhanced floral and woody notes and have excellent lasting scent properties and diffusibility compared with the fragrance compositions of Comparative Examples. This reveals that the alicyclic alcohol represented by Formula (1) of the present invention can impart high diffusibility to a fragrance composition and can further impart lasting scent properties compared with other materials having a floral and/or woody note(s), and thus is also useful as a fragrance ingredient. In addition, the fragrance composition containing the alicyclic alcohol represented by Formula (1) with excellent diffusibility is found to be useful as a perfuming component for various products.

Furthermore, as shown in Example 1, the alicyclic alcohol composition of the present invention containing the alicyclic alcohol represented by Formula (1) and the alicyclic alcohol represented by Formula (2) are also found to have a scent including floral notes of muguet, jasmine, and rose as well as a woody note in a lasting scent and to be useful as a fragrance.

The invention claimed is:

1. An alicyclic alcohol of formula (1):

(1)

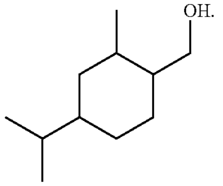

2. A fragrance composition, comprising:

the alicyclic alcohol of claim 1.

3. An alicyclic alcohol composition, comprising:

an alicyclic alcohol of formula (1):

(1)

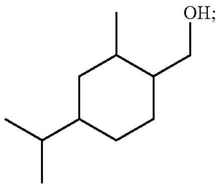

and an alicyclic alcohol of formula (2);

(2)

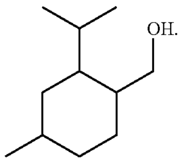

4. The alicyclic alcohol composition of claim 3, further comprising:

an alicyclic alcohol of formula (3):

(3)

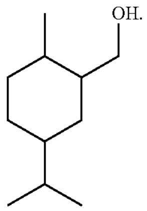

5. The alicyclic alcohol composition of claim 3, wherein a total content of the alicyclic alcohol of formula (1) and the alicyclic alcohol of formula (2) is 95 mass % or higher.

6. The alicyclic alcohol composition of claim 3, wherein the alicyclic alcohol of formula (1) is present in a range of from 85 to 98 mass %.

7. The alicyclic alcohol composition of claim 3, wherein a (1)/(2) mass ratio of the alicyclic alcohol of formula (1) and the alicyclic alcohol of formula (2) in the alicyclic alcohol composition is in a range of from 85/15 to 98/2.

8. A fragrance composition, comprising:

the alicyclic alcohol composition of claim 3.

9. An alicyclic alcohol of formula (2):

(2)

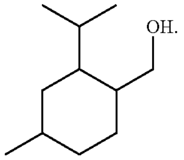

10. A fragrance composition, comprising:

the alicyclic alcohol of claim 9.

11. The fragrance composition of claim 2, having a complex scent comprising floral notes of muguet, jasmine, and rose as well as a soft woody note in a lasting scent.

12. The fragrance composition of claim 3, having a complex scent comprising floral notes of muguet, jasmine, and rose as well as a soft woody note in a lasting scent.

13. The fragrance composition of claim 8, having a complex scent comprising floral notes of muguet, jasmine, and rose as well as a soft woody note in a lasting scent.

14. The fragrance composition of claim 10, having a complex scent comprising floral notes of muguet, jasmine, and rose as well as a soft woody note in a lasting scent.

15. The fragrance composition of claim 3, wherein a (1)/(2) mass ratio of the alicyclic alcohol of formula (1) and the alicyclic alcohol of formula (2) in the alicyclic alcohol composition is in a range of from 87/13 to 97/3.

16. The alicyclic alcohol composition of claim 3, wherein a (1)/(2) mass ratio of the alicyclic alcohol of formula (1) and the alicyclic alcohol of formula (2) in the alicyclic alcohol composition is in a range of from 87/13 to 95/5.

17. The alicyclic alcohol composition of claim 3, wherein a (1)/(2) mass ratio of the alicyclic alcohol of formula (1) and the alicyclic alcohol of formula (2) in the alicyclic alcohol composition is in a range of from 90/10 to 95/5.

18. The alicyclic alcohol composition of claim 4, wherein the alicyclic alcohol of formula (3) is present in a range of from 0.1 to 3 mass %.

19. The alicyclic alcohol composition of claim 4, wherein the alicyclic alcohol of formula (3) is present in a range of from 1 to 2 mass %.

20. The alicyclic alcohol composition of claim 3, wherein the alicyclic alcohol of formula (2) is present in a range of from 2 to 15 mass %.

* * * * *